United States Patent
Janssens et al.

(10) Patent No.: US 7,994,173 B2
(45) Date of Patent: Aug. 9, 2011

(54) 2-PIPERAZIN-1-YL-3H-IMIDAZO [4,5-B]PYRIDINE DERIVATIVES

(75) Inventors: Frans Eduard Janssens, Beerse (BE); Jerome Emile Georges Guillemont, Val de Reuil Cedex (FR); Francois Maria Sommen, Beerse (BE); Jean-Francois Bonfanti, Val de Reuil Cedex (FR)

(73) Assignee: Janssen Pharmaceutica N.V., Beerse (BE)

( * ) Notice: Subject to any disclaimer, the term of this patent is extended or adjusted under 35 U.S.C. 154(b) by 192 days.

(21) Appl. No.: 12/523,936

(22) PCT Filed: Jan. 24, 2008

(86) PCT No.: PCT/EP2008/050818
§ 371 (c)(1),
(2), (4) Date: Jul. 21, 2009

(87) PCT Pub. No.: WO2008/090200
PCT Pub. Date: Jul. 31, 2008

(65) Prior Publication Data
US 2010/0004260 A1    Jan. 7, 2010

(30) Foreign Application Priority Data
Jan. 25, 2007    (EP) .................................... 07101153

(51) Int. Cl.
*A61K 31/496* (2006.01)
*A61P 1/14* (2006.01)
*C07D 471/04* (2006.01)

(52) U.S. Cl. .................................. 514/253.04; 544/362
(58) Field of Classification Search .................. None
See application file for complete search history.

(56) References Cited

U.S. PATENT DOCUMENTS 5,086,056 A * 2/1992 Janssens et al. ......... 514/252.16
2003/0139393 A1 * 7/2003 Janssens et al. ......... 514/217.07

FOREIGN PATENT DOCUMENTS

EP          512939    * 11/1992
WO        01/37824    *  5/2001

* cited by examiner

*Primary Examiner* — Emily Bernhardt
(74) *Attorney, Agent, or Firm* — Woodcock Washburn, LLP

(57) ABSTRACT

The present invention is concerned with novel compounds of formula (I) having fundic relaxating activity. The invention further relates to methods for preparing such compounds, pharmaceutical compositions comprising said compounds as well as the use as a medicine of said compounds.

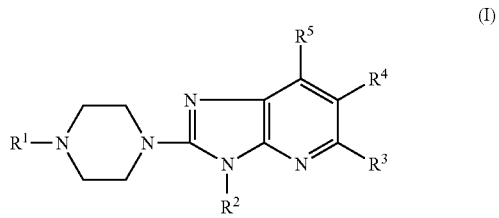

(I)

11 Claims, No Drawings

2-PIPERAZIN-1-YL-3H-IMIDAZO[4,5-B]PYRIDINE DERIVATIVES

CROSS-REFERENCE TO RELATED APPLICATIONS

This application is the National Stage of International Application No. PCT/EP2008/050818, filed Jan. 24, 2008, which claims the benefit of EP Application No. 07101153.0 filed Jan. 25, 2007, the disclosures of which are incorporated herein by reference in their entirety.

The present invention is concerned with novel compounds of formula (I) having fundic relaxating activity. The invention further relates to methods for preparing such compounds, pharmaceutical compositions comprising said compounds as well as the use as a medicine of said compounds.

EP-A-0,079,545 discloses piperazinyl substituted benzimidazole derivatives with antihistaminic activity. EP-0,397,613 discloses aminoimidazopyridines having antihistaminic activity and EP-0,512,939 discloses 2-piperazinylbenzimidazole derivatives as antagonists of serotonin $5HT_3$ receptors. EP-1,250,337 discloses substituted homopiperidinyl benzimidazole analogues as fundic relaxants.

The present invention concerns compounds of formula (I)

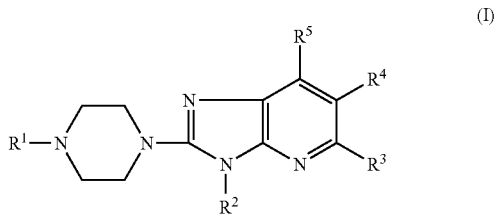

including any stereochemically isomeric form thereof, wherein
$R^1$ is hydrogen, phenylmethyl, pyridinylmethyl or benzo[1,3]dioxolylmethyl;
$R^2$ is $C_{1-4}$alkyl;
$R^3$ is hydrogen, halo or $C_{1-4}$alkyl;
$R^4$ is hydrogen, halo or $C_{1-4}$alkyl; and
$R^5$ is hydrogen, amino, $C_{1-4}$alkylamino or di($C_{1-4}$alkyl)amino;
or a pharmaceutically acceptable acid addition salt thereof, or a solvate thereof.

As used in the foregoing definitions:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

Interesting compounds of formula (I) are those compounds of formula (I) wherein one or more of the following restrictions apply:
a) $R^1$ is phenylmethyl; or
b) $R^1$ is pyridinylmethyl; or
c) $R^1$ is hydrogen; or
d) $R^2$ is methyl; or
e) $R^3$, $R^4$ and $R^5$ are hydrogen.

Compounds of formula (I) can in general be prepared by N-alkylating an intermediate of formula (II) with an intermediate of formula (III).

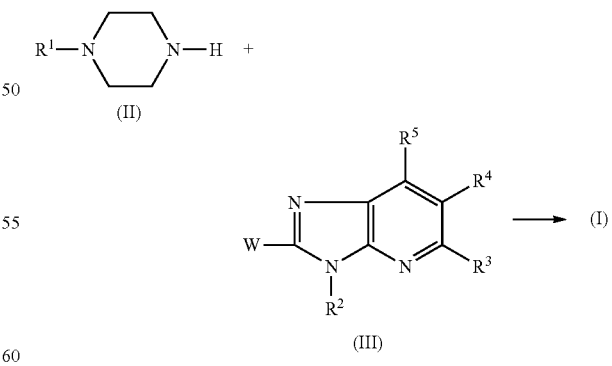

In formula (III) and hereinafter W represents an appropriate leaving group such as, for example, halo, e.g. chloro, bromo and the like; or a sulfonyloxy group such as, for example, methanesulfonyloxy, 4-methylbenzenesulfonyloxy and the like. Said N-alkylation reaction can conveniently be conducted in a reaction-inert solvent such as, for example, an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., tetrahydrofuran, 1,4-dioxane, 1,1'-oxybisethane and the like; a dipolar aprotic solvent, e.g., N,N-dimethylformamide, N,N-dimethylacetamide, dimethyl sulfoxide, nitrobenzene, 1-methyl-2-pyrrolidinone and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium tert. butoxide, sodium hydride, sodium amide, sodium hydroxide, calcium carbonate, calcium hydroxide, calcium oxide and the like; or an organic base, such as, for example, an amine, e.g., N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Alternatively, said N-alkylation may be carried out by applying art-known conditions of phase transfer catalysis reactions.

Compounds of formula (I) can also be prepared by N-alkylating a compound of formula (I-a) with an intermediate of formula (IV) wherein $R^{1'}$ is defined as radical $R^1$ other than hydrogen.

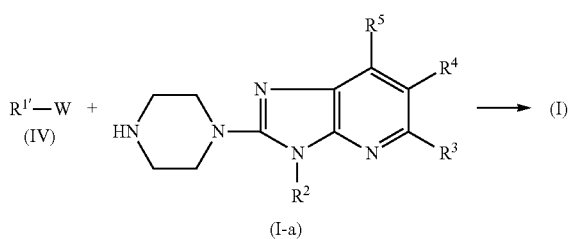

In formula (IV) and hereinafter W represents an appropriate leaving group such as, for example, halo, e.g. chloro, bromo and the like; or a sulfonyloxy group such as, for example, methanesulfonyloxy, 4-methylbenzenesulfonyloxy and the like. Said N-alkylation reaction can conveniently be conducted as described above.

Compounds of formula (I-a), defined as compounds of formula (I) wherein $R^1$ represents hydrogen, can be prepared by hydrogenating compounds of formula (I-b), defined as compounds of formula (I) wherein $R^1$ represents phenylmethyl, in the presence of a suitable catalyst such as palladium-on-carbon.

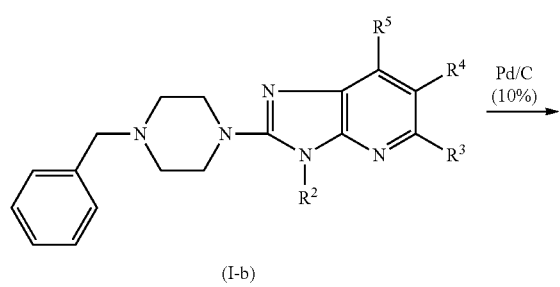

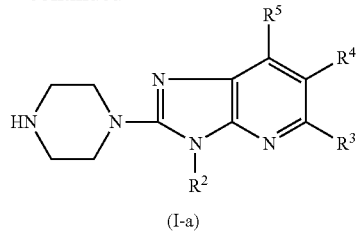

Intermediates of formula (III) are known such as 2-chloro-3-ethyl-3H-imidazo[4,5-b]pyridine (Bollettino Chimico Farmaceutico (1970), 109, (11), 665-73), or are prepared as set out in the Examples A.1, A.2, A3, A.4, A.5 and A.6.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereo specifically. Preferably if a specific stereoisomer is desired, said compound will be synthesized by stereospecific methods of preparation. These methods will advantageously employ enantiomerically pure starting materials.

In view of the capability of the compounds of the present invention to relax the fundus as demonstrated in Pharmacological Example C.1, the subject compounds are useful to treat conditions related to a hampered or impaired relaxation of the fundus such as, e.g. gastro-oesophageal reflux, heartburn (including episodic heartburn, nocturnal heartburn, and meal-induced heartburn), dyspepsia, early satiety, bloating and anorexia.

Dyspepsia may be caused by delayed gastric emptying, by impaired relaxation of the fundus to food ingestion or by hypersensitivity to gastric relaxation. Dyspeptic symptoms are for example a lack of appetite, feeling of fullness, early satiety, nausea, vomiting, bloating and gaseous eructation.

Warm-blooded animals, including humans, (generally called herein patients) suffering from dyspeptic symptoms as a result of delayed gastric emptying usually have a normal fundic relaxation and can be relieved of their dyspeptic symptoms by administering a prokinetic agent such as, e.g. cisapride.

Patients can have dyspeptic symptoms without having a disturbed gastric emptying. Their dyspeptic symptoms may result from a hypercontracted fundus resulting in a diminished compliance and abnormalities in the adaptive fundic relaxation. Also dyspeptic symptoms may arise from hypersensitivity of the fundus to relaxation.

A hypercontracted fundus results in a diminished compliance of the stomach. The "compliance of the stomach" can be expressed as the ratio of the volume of the stomach over the pressure exerted by the stomach wall. The compliance of the stomach relates to the gastric tone, which is the result of the tonic contraction of muscle fibers of the proximal stomach.

This proximal part of the stomach, by exerting a regulated tonic contraction (gastric tone), accomplishes the reservoir function of the stomach.

Patients suffering from early satiety cannot finish a normal meal since they feel saturated before they are able to finish said normal meal. Normally when a subject starts eating, the stomach will show an adaptive relaxation, i.e. the stomach will relax to accept the food that is ingested. This adaptive relaxation is not possible when the compliance of the stomach is hampered which results in an impaired relaxation of the fundus.

In view of the utility of the compounds of formula (I), it follows that the present invention also provides a method of treating warm-blooded animals, including humans, (generally called herein patients) suffering from impaired relaxation of the fundus to food ingestion. Consequently a method of treatment is provided for relieving patients suffering from conditions, such as, for example, gastro-oesophageal reflux, heartburn (including episodic heartburn, nocturnal heartburn, and meal-induced heartburn), dyspepsia, early satiety, bloating and anorexia.

Hence, the use of a compound of formula (I) as medicine is provided, and in particular the use of a compound of formula (I) for the manufacture of a medicine for treating conditions involving an impaired relaxation of the fundus to food ingestion such as e.g. gastro-oesophageal reflux, heartburn (including episodic heartburn, nocturnal heartburn, and meal-induced heartburn), dyspepsia, early satiety, bloating and anorexia. Both prophylactic and therapeutic treatment are envisaged.

The symptoms of impaired fundic relaxation may also arise due to the intake of chemical substances, e.g. Selective Seretonine Re-uptake Inhibitors (SSRI's), such as fluoxetine, paroxetine, fluvoxamine, citalopram, sertraline; or erythromycin and erythromycin alike antibiotic macrolides such as, e.g. EM-523, EM-574, ABT-229, GM-611, (8R)-4"-deoxy-6,9-epoxyerythromycin A, (8S)-4"-deoxy-6,9-epoxyerythromycin A, A-81648, A-173508, A-182061, and KC-11458.

Another functional gastrointestinal disorder is irritable bowel syndrome whereby one of its features is believed to be related to hypersensitivity of the gut to distension. Hence it is therefore believed that modulation of said hypersensitivity by the compounds of the present invention having fundus relaxation properties may result in a reduction of the symptoms in subjects suffering from IBS. Accordingly the use of a compound of formula (I) for the manufacture of a medicine for treating IBS (irritable bowel syndrome) is provided. Furthermore the compounds of formula (I) are also able to reduce the pain associated with gastrointestinal hypersensitivity.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

Those of skill in the treatment of conditions related to a hampered or impaired relaxation of the fundus could easily determine the effective daily amount from the test results presented hereinafter. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.1 mg to 350 mg, and in particular 1 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9 by weight %, even more preferably from 50 to 99.9 by weight % of a pharmaceutically acceptable carrier, all percentages being based on the total composition.

EXPERIMENTAL PART

In the procedures described hereinafter the following abbreviations were used: 'DCM' stands for dichloromethane; 'DMF' means N,N-dimethylformamide; DIPE stands for diisopropylether. For some chemicals the chemical formula was used, e.g. $CH_2Cl_2$ stands for dichloromethane; $NH_4OH$ means ammonium hydroxide, $CH_3OH$ means methanol, $K_2CO_3$ means potassium carbonate; and $MgSO_4$ means magnesium sulfate.

A. Synthesis of the Intermediates

Example A.1 a) Preparation of

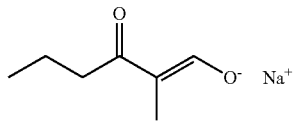

intermediate (1)

3-Hexanone (1.627 mol) and ethyl formate (1.79 mol) were added slowly at 5° C. to a solution of sodium methanolate (30%) (1.79 mol) in diethyl ether (1500 ml). The mixture was stirred at room temperature for 18 hours (precipitation resulted). The solvent was evaporated till dryness. The product was used without further purification, yielding 260 g of intermediate (1).

b) Preparation of

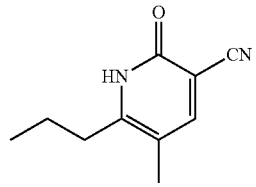

intermediate (2)

A mixture of intermediate (1) (1.732 mol), 2-cyanoacetamide (0.868 mol) and piperidinium acetate (0.65 mol) in water (1500 ml) was stirred and refluxed for 8 hours. Acetic acid (200 ml) was added. The precipitate was filtered off, washed with water and dried, yielding 85 g (27%) of product. A part (3 g) was crystallized from 2-propanone and DIPE. The precipitate was filtered off and dried, yielding 1.5 g of intermediate (2) (mp. 220° C.).

c) Preparation of

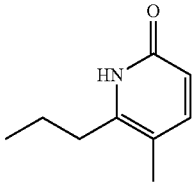

intermediate (3)

A mixture of intermediate (2) in hydrochloric acid (1000 ml) was stirred and refluxed for 6 days, then poured out on ice, basified with NH₄OH and extracted with DCM. The organic layer was separated, dried (MgSO₄), filtered and the solvent was evaporated, yielding 31 g of residue. A part (1 g) was crystallized from a mixture of 2-propanone and DIPE. The precipitate was filtered off and dried, yielding 0.3 g of intermediate (3) (mp. 101° C.).

d) Preparation of

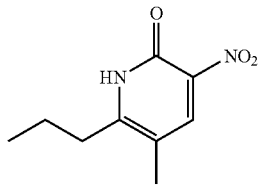

intermediate (4)

Nitric acid (0.37 mol) was added slowly at 5° C. to a solution of intermediate (3) (0.185 mol) in sulphuric acid (280 ml). The mixture was stirred at 5° C. for 1 hour, poured out on ice and extracted with DCM. The organic layer was separated, dried (MgSO₄), filtered and the solvent was evaporated, yielding 25.6 g of residue. A part (1 g) was crystallized from acetonitrile and DIPE. The precipitate was filtered off and dried, yielding 0.5 g of intermediate (4) (mp. 218° C.).

e) Preparation of

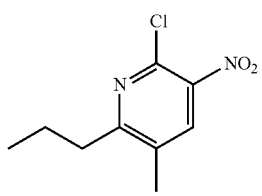

intermediate (5)

Phosphoric trichloride (0.595 mol) was added slowly at room temperature to a solution of intermediate (4) and N,N,N-triethylbenzenemethanaminium chloride (0.06 mol) in acetonitrile (400 ml). The mixture was stirred at 80° C. for 8 hours. The solvent was evaporated. The residue was poured out on ice. The mixture was basified with NH₄OH and extracted with DCM. The organic layer was separated, dried (MgSO₄), filtered and the solvent was evaporated. The product was used without further purification, yielding 26 g of intermediate (5).

f) Preparation of

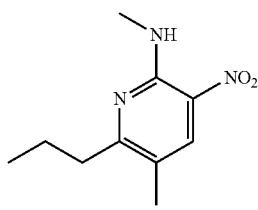

intermediate (6)

A mixture of intermediate (5) (0.093 mol) in a solution of methanamine in water (40%) (100 ml) was stirred at room temperature overnight and poured out into ice water. The precipitate was filtered, washed with water and dried, yielding 17 g (87%) of intermediate (6) (mp. 97° C.).

g) Preparation of

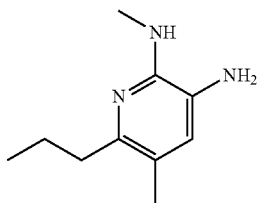

intermediate (7)

A mixture of intermediate (6) (0.0812 mol) and Raney nickel (20 g) in methanol (200 ml) was stirred at room temperature for 2 hours under a 3 bar pressure of hydrogen, then filtered over celite. Celite was washed with water. The filtrate was evaporated till dryness, yielding 14.5 g of intermediate (7).

h) Preparation of

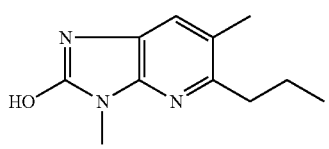

intermediate (8)

A mixture of intermediate (7) (0.082 mol) and urea (0.089 mol) in xylene (150 ml) was stirred and refluxed overnight, then cooled to room temperature. The precipitate was filtered, washed with water and dried. The residue was purified by column chromatography over silica gel (eluent: CH₂Cl₂/CH₃OH/NH₄OH 97/3/0.5; 15-355 µm). The pure fractions were collected and the solvent was evaporated. The residue was crystallized from acetonitrile/DIPE. The precipitate was filtered off and dried, yielding 0.9 g (5.5%) of intermediate (8) (mp. 230° C.).

i) Preparation of

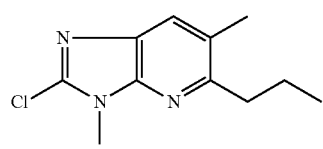

intermediate (9)

Hydrochloric acid (2N) (2 ml) was added very slowly at 100° C. to a mixture of intermediate (8) (0.053 mol) in phosphoric trichloride (100 ml). The mixture was stirred at 120° C. overnight, then cooled and the solvent was evaporated. The residue was taken up in an aqueous K$_2$CO$_3$ solution (10%) and extracted with CH$_2$Cl$_2$/CH$_3$OH (95/5). The organic layer was separated, dried (MgSO$_4$), filtered, and the solvent was evaporated till dryness, yielding 8.5 g (72%) of intermediate (9).

Example A.2 a) Preparation of

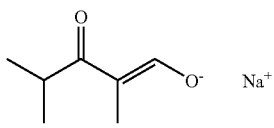
intermediate (10)

2-Methyl-3-pentanone (0.998 mol) and ethyl formate (1.098 mol) were added slowly at 5° C. to a solution of sodium methanolate (30%) (1.098 mol) in diethyl ether (1000 ml). The mixture was stirred at room temperature for 8 hours. The solvent was evaporated. The product was used without further purification, yielding intermediate (10).

b) Preparation of

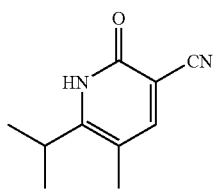
intermediate (11)

Intermediate (10) (0.998 mol) and 2-cyanoacetamide (0.998 mol) were added to a solution of piperidinium acetate (0.749 mol) in water (1000 ml). The mixture was stirred and refluxed for 8 hours. Acetic acid (150 ml) was added. The precipitate was filtered off, washed with water and dried, yielding 44 g of product as fraction (1). A part of said fraction (1) (2 g) was crystallized from diethyl ether. The precipitate was filtered off and dried, yielding 1.3 g of intermediate (11) (mp. 241° C.).

c) Preparation of

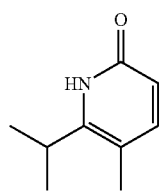
intermediate (12)

A mixture of intermediate (11) (0.238 mol) in hydrochloric acid (6N) (400 ml) was stirred and refluxed for 6 days, then poured out on ice and basified with NH$_4$OH. The precipitate was filtered off, washed with water and dried, yielding fraction (1). The filtrate was extracted with CH$_2$Cl$_2$/CH$_3$OH 90/10. The organic layer was separated, dried (MgSO$_4$), filtered and the solvent was evaporated. The residue was combined with fraction (1), yielding 33 g of product. Part of this product (3 g) was crystallized from diethyl ether. The precipitate was filtered off and dried, yielding 2.6 g of intermediate (12) (mp. 197° C.).

d) Preparation of

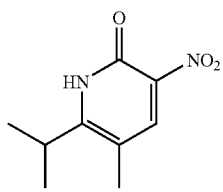
intermediate (13)

Nitric acid (0.391 mol) was added slowly at 5° C. to a solution of intermediate (12) (0.198 mol) in sulphuric acid (300 ml) while the temperature was kept below 15° C. The mixture was stirred at 5° C. for 1 hour and poured out on ice. The precipitate was filtered off, washed with water and dried, yielding fraction (1). The filtrate was extracted with DCM. The organic layer was separated, dried (MgSO$_4$), filtered and the solvent was evaporated. The residue was combined with the fraction (1), yielding 35 g of intermediate (13).

e) Preparation of

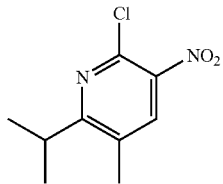
intermediate (14)

Phosphoric trichloride (0.505 mol) was added slowly at room temperature to a solution of intermediate (13) (0.168 mol) and N,N,N-triethylbenzenemethanaminium chloride (0.084 mol) in acetonitrile (350 ml). The mixture was stirred at 80° C. for 8 hours. The solvent was evaporated till dryness. The residue was taken up on ice. The mixture was basified with NH$_4$OH and extracted with DCM. The organic layer was separated, dried (MgSO$_4$), filtered and the solvent was evaporated, yielding 37 g of intermediate (14).

f) Preparation of

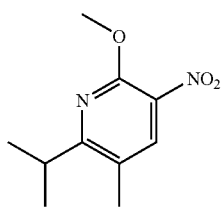
intermediate (15)

Sodium methanolate (30%) (0.517 mol) was added slowly at room temperature to a solution of intermediate (14) (0.172 mol) in methanol (350 ml). The mixture was stirred at room temperature for 8 hours, poured out on ice and extracted with DCM. The organic layer was separated, dried ($MgSO_4$), filtered and the solvent was evaporated, yielding 32 g of intermediate (15).

g) Preparation of

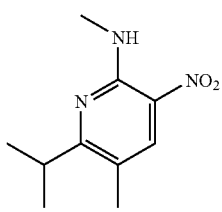

intermediate (16)

A mixture of intermediate (15) (0.055 mol) in methanamine (200 ml) was stirred at 100° C. for 48 hours, then cooled. Ice was added. The precipitate was filtered, washed with water and dried, yielding 11.45 g of intermediate (16). This product was used directly in the next reaction step.

h) Preparation of

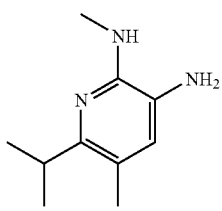

intermediate (17)

A mixture of intermediate (16) (0.055 mol) and Raney nickel (15 g) in methanol (150 ml) was stirred at room temperature for 1 hour under a 3 bar pressure of hydrogen, then filtered over celite. Celite was washed with water. The filtrate was evaporated till dryness, yielding 10 g of intermediate (17)

i) Preparation of

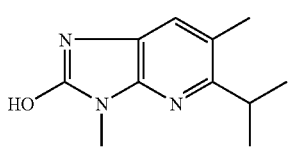

intermediate (18)

A mixture of intermediate (17) (0.055 mol) and urea (0.066 mol) in xylene (100 ml) was stirred and refluxed overnight, then cooled. The precipitate was filtered, washed with DIPE and dried, yielding 7.5 g of intermediate (18).

j) Preparation of

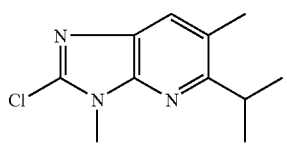

intermediate (19)

A mixture of intermediate (18) (0.0365 mol) in phosphoric trichloride (75 ml) was stirred at 100° C. Hydrochloric acid (12N) (0.75 ml) was added dropwise very carefully. The mixture was stirred at 120° C. overnight. The solvent was evaporated till dryness. The residue was taken up on ice, saturated with $K_2CO_3$ and extracted with $CH_2Cl_2/CH_3OH$ (95/5). The organic layer was separated, dried ($MgSO_4$), filtered, and the solvent was evaporated till dryness, yielding 9 g of intermediate (19).

Example A.3 a) Preparation of

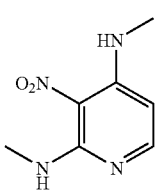

intermediate (20)

A mixture of 2-chloro-4-methoxy-3-nitropyridine (0.0509 mol) in methanamine in water (40%) (100 ml) was stirred at 60° C. for 2 hours, then poured out into ice water. The precipitate was filtered, washed with water and dried, yielding 9.1 g of intermediate (20) (mp. 156° C.).

b) Preparation of

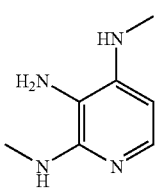

intermediate (21)

A mixture of intermediate (20) (0.0764 mol) and Raney nickel (15 g) in methanol (150 ml) was stirred for 2 hours under a 3 bar pressure of hydrogen. The precipitate was filtered over celite. The filtrate was evaporated till dryness, yielding 10.8 g of intermediate (21).

c) Preparation of

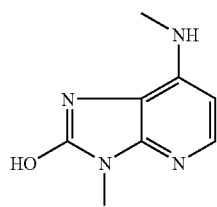
intermediate (22)

A mixture of intermediate (21) (0.07 mol) and urea (0.084 mol) in xylene (100 ml) was stirred at 160° C. overnight, then cooled to room temperature. The precipitate was filtered, washed with DIPE and dried. The residue was purified by column chromatography over silica gel (eluent: $CH_2Cl_2$/$CH_3OH$ 93/7; 15-35 μm). Three fractions were collected and the solvent was evaporated. Fraction (1) (0.6 g) was crystallized from acetonitrile/DIPE. The precipitate was filtered off and dried, yielding 0.47 g of intermediate (22) (mp. >260° C.).

d) Preparation of

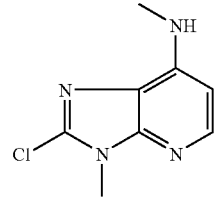
intermediate (23)

Intermediate (22) (0.028 mol) in phosphoric trichloride (100 ml) was stirred at 100° C. Hydrochloric acid (12N) (2 ml) was added dropwise slowly. The mixture was stirred and refluxed overnight. The solvent was evaporated till dryness. The residue was taken up on ice, basified with $K_2CO_3$ 10% and extracted with $CH_2Cl_2$/$CH_3OH$. The organic layer was separated, dried ($MgSO_4$), filtered, and the solvent was evaporated till dryness, yielding 9.9 g of intermediate (23).

Example A.4 a) Preparation of

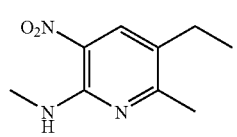
intermediate (24)

A mixture of 2-chloro-5-ethyl-6-methyl-3-nitropyridine (0.0747 mol) in methanamine (0.249 mol) was stirred at 80° C. overnight and poured out into ice water. The precipitate was filtered, washed with water and dried, yielding 15.2 g of intermediate (24) (mp. 124° C.).

b) Preparation of

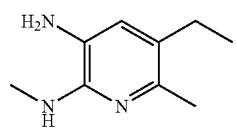
intermediate (25)

A mixture of intermediate (24) (0.046 mol) and Raney nickel (10 g) in methanol (100 ml) was hydrogenated at room temperature for 2 hours under a 3 bar pressure. Raney nickel was eliminated by filtration over celite. The filtrate was evaporated till dryness, yielding 7.7 g of intermediate (25).

c) Preparation of

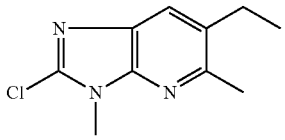
intermediate (26)

A mixture of intermediate (25) (0.046 mol) and urea (0.0552 mol) in xylene (80 ml) was stirred and refluxed overnight and cooled to room temperature. The precipitate was filtered, washed with DIPE and dried. The residue was purified by column chromatography over silica gel (eluent: $CH_2Cl_2$/$CH_3OH$ 96/4; 15-35 μm). Two fractions were collected and the solvent was evaporated. The residue was crystallized from acetonitrile/DIPE. The precipitate was filtered off and dried, yielding 5.8 g of product. The product was crystallized from acetonitrile/DIPE. The precipitate was filtered off and dried, yielding 0.85 g of intermediate (26) (mp. 121° C.).

d) Preparation of intermediate (27)

A mixture of intermediate (26) (0.027 mol) in phosphoric trichloride (40 ml) was stirred at 100° C. Hydrochloric acid (12N) (0.8 ml) was added slowly. The mixture was stirred and refluxed overnight, cooled and evaporated till dryness. The residue was taken up in ice water, saturated by $K_2CO_3$ and extracted with $CH_2Cl_2$/$CH_3OH$: 95/5. The organic layer was separated, dried ($MgSO_4$), filtered, and the solvent was evaporated, yielding 3.6 g of intermediate (27).

Example A.5 a) Preparation of

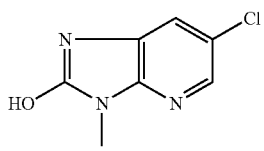

intermediate (28)

A mixture of 3-amino-5-chloro-2-methylaminopyridine (0.117 mol) and urea (0.129 mol) in xylene (150 ml) was stirred and refluxed overnight. The solvent was evaporated till dryness. The residue was taken up in DCM. The organic layer was separated, washed with water, dried (MgSO$_4$), filtered and the solvent was evaporated till dryness. The residue was purified by column chromatography over silica gel (eluent: CH$_2$Cl$_2$/CH$_3$OH 98/2; 15-35 μm). Two fractions were collected and the solvent was evaporated, yielding 0.5 g of fraction (1) and 18 g (86%) of fraction (2). Fraction (1) was crystallized from 2-propanone/acetonitrile/DIPE. The precipitate was filtered off and dried, yielding 0.4 g of intermediate (28).

b) Preparation of

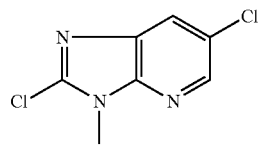

intermediate (29)

A mixture of intermediate (28) (0.098 mol) in phosphoric trichloride (180 ml) was stirred at 100° C. Hydrochloric acid (12N) (2 ml) was added dropwise very carefully. The mixture was stirred and refluxed overnight. The solvent was evaporated till dryness. The residue was poured out on ice, saturated with K$_2$CO$_3$ and extracted with CH$_2$Cl$_2$/CH$_3$OH (95/5). The organic layer was separated, dried (MgSO$_4$), filtered, and the solvent was evaporated till dryness, yielding 12.5 g of intermediate (29).

Example A. 6

Preparation of

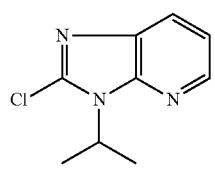

intermediate (30)

Hydrochloric acid (1.5 ml) was added dropwise very carefully at 100° C. to a mixture of 1,3-dihydro-3-isopropyl-2H-imidazo[4,5-b]pyridin-2-one (0.0846 mol) in phosphoric trichloride (150 ml). The mixture was stirred at 120° C. overnight and the solvent was evaporated till dryness. The residue was poured out on ice, saturated with K$_2$CO$_3$ and extracted with DCM. The organic layer was separated, dried (MgSO$_4$), filtered, and the solvent was evaporated till dryness, yielding 14 g of intermediate (30).

B. Preparation of the Final Compounds

Example B.1

Preparation of

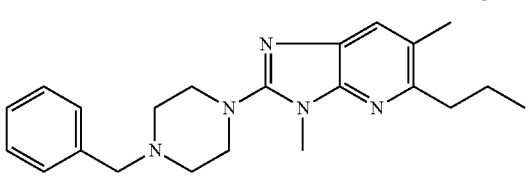

compound (1)

A mixture of intermediate (9) (0.038 mol) and 1-(phenylmethyl)piperazine (0.057 mol) was stirred at 120° C. for 3 hours, then taken up in DCM. The precipitate was filtered. The filtrate was evaporated till dryness. The residue (17 g) was purified by column chromatography over silica gel (eluent: CH$_2$Cl$_2$/CH$_3$OH/NH$_4$OH 95/5/0.1; 15-35 μm). The pure fractions were collected and the solvent was evaporated, yielding 1.3 g of residue. The residue was crystallized from 2-propanone/acetonitrile/DIPE. The precipitate was filtered off and dried, yielding 1.25 g of compound (1) (mp. 127° C.).

Compound (2) was prepared analogously by replacing intermediate (9) with intermediate (23).

Compound (5) was prepared analogously by replacing intermediate (9) with intermediate (30).

Compound (6) was prepared analogously by replacing intermediate (9) with intermediate (19).

Compound (7) was prepared analogously by replacing intermediate (9) with 2-chloro-3-ethyl-3H-imidazo[4,5-b]pyridine.

Compound (8) was prepared analogously by replacing intermediate (9) with intermediate (27).

Compound (13) was prepared analogously by replacing intermediate (9) with intermediate (29).

Example B.2

Preparation of

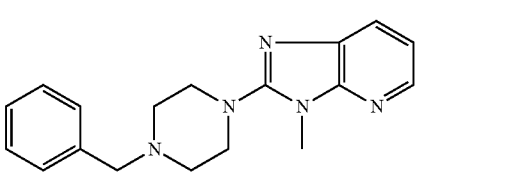

compound (11)

A mixture of 2-chloro-3-methyl-3H-imidazo[4,5-b]pyridine (0.0335 mol) and 1-(phenylmethyl)piperazine (0.0505 mol) was stirred at 120° C. for 1 hour. A mixture of an aqueous K$_2$CO$_3$ (10%) solution and DCM was added. The mixture was stirred at room temperature for 10 minutes. The organic layer was separated, rinsed with DCM, dried (MgSO₄), filtered and the solvent was evaporated. The residue (35 g) was purified by column chromatography over silica gel (eluent: CH₂Cl₂/CH₃OH/NH₄OH; 96/3/0.1; 15-35 μm). Four fractions were collected and the solvent was evaporated. The residue was purified by column chromatography over silica gel (eluent: CH₂Cl₂/CH₃OH/NH₄OH; 98/2/0.1; 15-40 μm). The pure fractions were collected and the solvent was evaporated. The residue (1.5 g) was crystallized from DIPE. The precipitate was filtered off and dried, yielding 1 g of compound (11) (mp. 98° C.).

Example B.3 b) Preparation of compound (3)

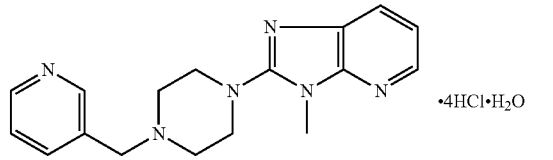

·4HCl·H₂O

A mixture of intermediate (31) (0.005 mol), 2-(chloromethyl)pyridine hydrochloride (1:1) (0.006 mol) and N,N-diethylethanamine (0.0253 mol) in DMF (60 ml) was stirred at 40° C. overnight. The solvent was evaporated till dryness. The residue was taken up in DCM/CH₃OH. The precipitate was washed with an aqueous K₂CO₃ (10%) solution. The organic layer was separated, dried (MgSO₄), filtered and the solvent was evaporated till dryness. The residue (2.3 g) was purified by column chromatography over silica gel (eluent: CH₂Cl₂/CH₃OH/NH₄OH 96/4/0.4; 15-40 μm), yielding 1.5 g (96%). This fraction was dissolved in 2-propanol/HCl 5N and converted into the hydrochloric acid salt. The precipitate was filtered off and dried. The residue was crystallized from ethanol/DIPE. The precipitate was filtered off and dried, yielding 1.7 g of compound (3) (mp. 182° C.).

Example B.4

Preparation of compound (9)

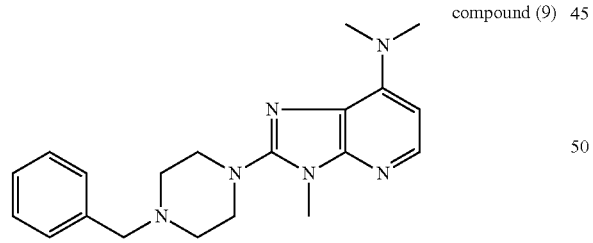

Sodium cyanotrihydroborate (0.036 mol) then acetic acid (4 ml) were added dropwise to a mixture of compound (2) (0.012 mol) and formaldehyde (0.12 mol) in acetonitrile (80 ml) under nitrogen flow. The mixture was stirred at room temperature overnight. Acetic acid (4 ml) was added. The mixture was stirred at 40° C. for 12 hours, then cooled to room temperature. An aqueous K₂CO₃ (10%) solution was added. The mixture was extracted with DCM. The organic layer was separated, dried (MgSO₄), filtered, and the solvent was evaporated till dryness. The residue was taken up in CH₃OH (80 ml). 2-Propanol and HCl 5N (10 ml) were added. The mixture was stirred and refluxed overnight. The solvent was evaporated till dryness. The residue was taken up in DCM and washed with an aqueous K₂CO₃ (10%) solution. The organic layer was separated, dried (MgSO₄), filtered, and the solvent was evaporated till dryness. The residue (4 g) was purified by column chromatography over silica gel (eluent: CH₂Cl₂/CH₃OH/NH₄OH 97/3/0.1; 15-40 μm). The pure fractions were collected and the solvent was evaporated. The residue (3.1 g) was crystallized from 2-propanone/acetonitrile/DIPE. The precipitate was filtered off and dried, yielding 2.7 g of compound (9) (mp. 128° C.).

Example B.5

Preparation of compound (10)

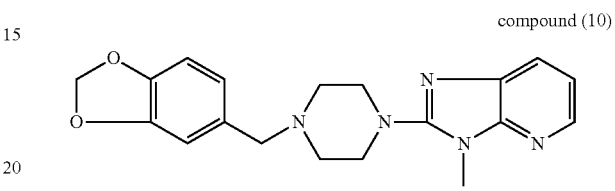

A mixture of the hydrochloric acid salt of intermediate (31) (0.0046 mol), 5-(chloromethyl)-1,3-benzodioxole (0.005 mol) and potassium carbonate (0.007 mol) in acetonitrile (80 ml) was stirred at 80° C. for 4 hours and the solvent was evaporated. The residue was taken up in a mixture of water and DCM. The organic layer was separated, dried (MgSO₄), filtered and the solvent was evaporated. The residue (2 g) was purified by column chromatography over silica gel (eluent: CH₂Cl₂/CH₃OH/NH₄OH 97/3/0.1; 15-40 μm). The pure fractions were collected and the solvent was evaporated. The residue (0.95 g) was crystallized from 2-propanone/DIPE. The precipitate was filtered off and dried, yielding 0.51 g of compound (10) (mp. 114° C.).

Example B.6

Preparation of compound (14)

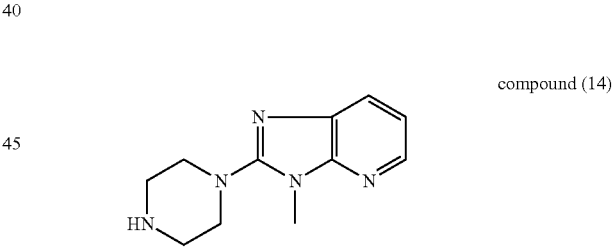

A mixture of compound (11) (0.0153 mol) and palladium-on activated carbon (1.4 g) in methanol (70 ml) was stirred at 50° C. for 12 hours under a 5 bar pressure of hydrogen, then cooled, filtered over celite, rinsed with methanol and concentrated. The residue (8 g) was purified by column chromatography over silica gel (eluent: CH₂Cl₂/CH₃OH/NH₄OH 90/10/1; 15-40 μm). The pure fractions were collected and the solvent was evaporated, yielding 5 g of compound (14) (mp. 136° C.). Compounds (15) and (16) were prepared using the same methodology starting from compounds (7) and (5) respectively however the column chromatography purification step was replaced by dissolving the residue in 2-propanol saturated with HCl in order to obtain the hydrochloric acid addition salt of said compounds (15) and (16) as a precipitate.

Table F-1 lists the compounds that were prepared according to one of the above Examples. The term ".C₂H₂O₄" stands for the ethanedioate salt.

TABLE F-1
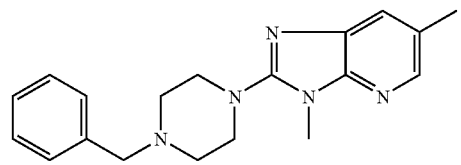
Co. No. 1; Ex. B.1; mp. 127° C.
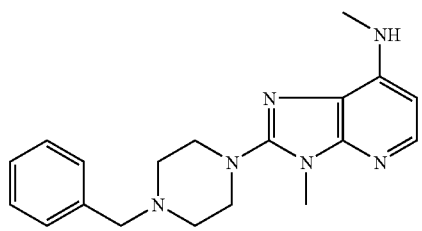
Co. No. 2; Ex. B.1; mp. 138° C.
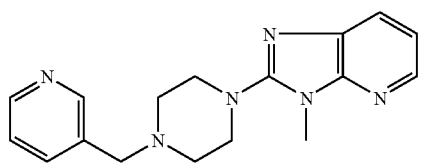
Co. No. 3; Ex. B.3; •4HCl•H$_2$O; mp. 185° C.
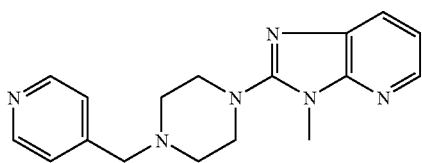
Co. No. 4; Ex. B.2; mp. 156° C.
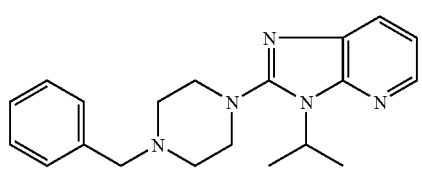
Co. No. 5; Ex. B.1; •5/2C$_2$H$_2$O$_4$; mp. 124° C.
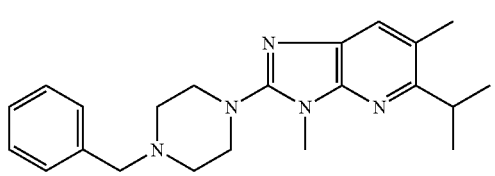
Co. No. 6; Ex. B.1; mp. 131° C.
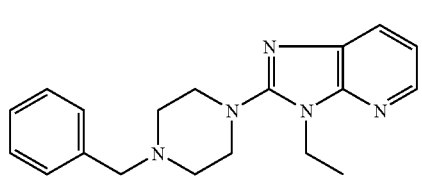
Co. No. 7; Ex. B.1; •2C$_2$H$_2$O$_4$; mp. 215° C.
TABLE F-1-continued
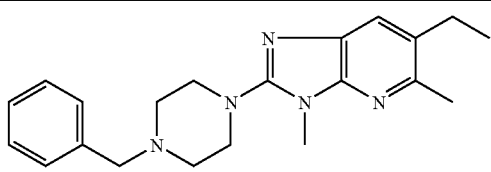
Co. No. 8; Ex. B.1; mp. 83° C.
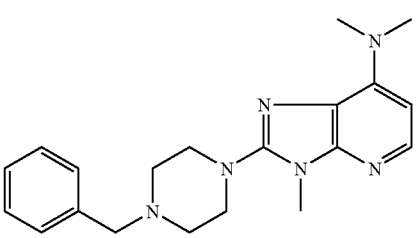
Co. No. 9; Ex. B.4; mp. 128° C.
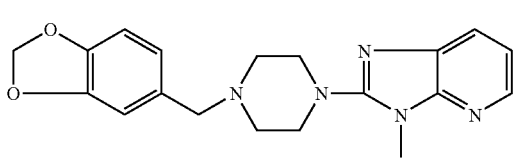
Co. No. 10; Ex. B.5; mp. 114° C.
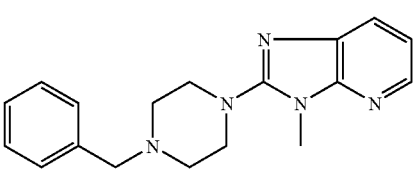
Co. No. 11; Ex. B.2; mp. 98° C.
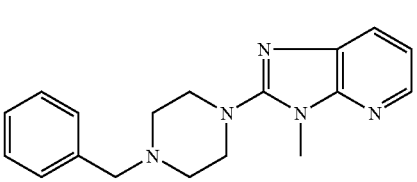
Co. No. 12; Ex. B.2; •HCl
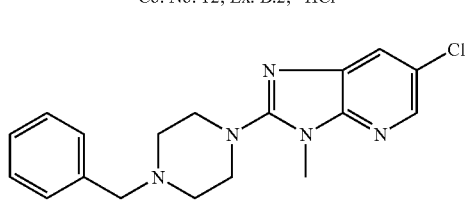
Co. No. 13; Ex. B.1; mp. 150° C.
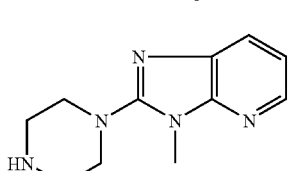
Co. No. 14; Ex. B.6; mp. 136° C.

TABLE F-1-continued

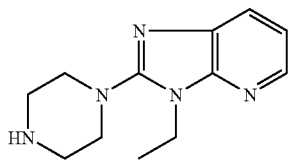

Co. No. 15; Ex. B.6; •HCl; mp. 162° C.

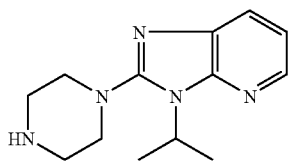

Co. No. 16; Ex. B.6; •HCl; mp. 162° C.

C. Pharmacological Examples

C.1. Gastric Tone Measured by an Electronic Barostat in Conscious Dogs

Gastric tone cannot be measured by manometric methods. Therefore an electronic barostat was used. This allows the study of the physiological pattern and regulation of gastric tone in conscious dogs and the influence of test-compounds on this tone.

The barostat consists of an air injection system which is connected by a double-lumen 14-French polyvinyl tube to an ultrathin flaccid polyethylene bag (maximal volume: ±700 ml). Variations in gastric tone were measured by recording changes in the volume of air within an intragastric bag, maintained at a constant pressure. The barostat maintains a constant pressure (preselected) within a flaccid air-filled bag introduced into the stomach, changing the volume of air within the bag by an electronic feedback system.

Thus, the barostat measures gastric motor activity (contraction or relaxation) as changes in intragastric volume (decrease or increase resp.) at a constant intragastric pressure. The barostat consists of a strain gauge linked by an electronic relay to an air injection-aspiration system. Both the strain gauge and the injection system are connected by means of double-lumen polyvinyl tube to an ultrathin polyethylene bag. A dial in the barostat allows selection of the pressure level to be maintained within the intragastric bag.

Female beagle dogs, weighing 7-17 kg, were trained to stand quietly in Pavlov frames. They were implanted with a gastric cannula under general anaesthesia and aseptic precautions. After a median laparotomy, an incision was made through the gastric wall in longitudinal direction between the greater and the lesser curve, 2 cm above the nerves of Latarjet. The cannula was secured to the gastric wall by means of a double purse string suture and brought out via a stub wound at the left quadrant of the hypochondrium. Dogs were allowed a recovery period of two weeks.

At the beginning of the experiment, the cannula was opened in order to remove any gastric juice or food remnants. If necessary, the stomach was cleansed with 40 to 50 ml lukewarm water. The ultrathin bag of the barostat was positioned into the fundus of the stomach through the gastric cannula. In order to ensure easy unfolding of the intragastric bag during the experiment, a volume of 150-200 ml was injected into the bag by raising the pressure to maximally 14 mm Hg (about 1.87 kPa) very briefly. This procedure was repeated twice.

After a stabilization period of 60 minutes at an intragastric pressure of 6 mmHg (about 0.81 kPa), the test compound was administered subcutaneously, or intraduodenally, at 2 mmHg (0.27 kPa). Test compounds were screened, i.e. changes in gastric volume are measured, at 0.63 mg/kg s.c. Other doses and routes were tested if a test compound was shown to be active during the screening procedure. Table C-1 summarizes the mean maximal change in volume (in ml) on relaxation of the fundus, 1 hour after I.D. administration of the test compound (0.63 mg/kg).

TABLE C-1

| Co. No. | Maximum change in volume (mean) |
| --- | --- |
| Co. No. 1 | 237 |
| Co. No. 2 | 220 |
| Co. No. 3 | 154 |
| Co. No. 4 | 112 |
| Co. No. 5 | 206 |
| Co. No. 6 | 206 |
| Co. No. 7 | 167 |
| Co. No. 8 | 239 |
| Co. No. 9 | 185 |
| Co. No. 10 | 251 |
| Co. No. 11 | 220 |
| Co. No. 13 | 247 |
| Co. No. 14 | 154.6(*) |
| Co. No. 15 | 78.3(*) |
| Co. No. 16 | 22.3(*) |

(*)administered at 0.16 mg/kg

Compound (11) was tested at different concentrations and the results are reported Table C-2 below and compared with compound (72) of WO-01/46189. Both compounds were administered I.D.

TABLE C-2

| | Dose mg/kg | | | | |
| --- | --- | --- | --- | --- | --- |
| Compound | 0.63 | 0.16 | 0.04 | 0.01 | 0.0025 |
| (11) of present invention | 220 | 180 | 146 | 157 | 83 |
| (72) of WO-01/46189 | | 45 | — | — | — |

Structure comparison:
(11) of present invention

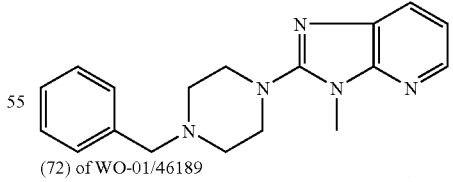

(72) of WO-01/46189

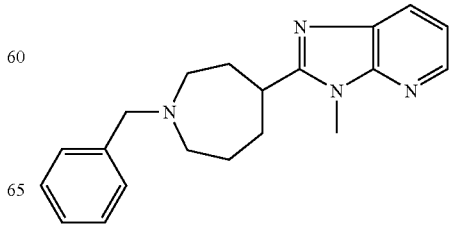

•HCl (1:2)

The invention claimed is:
1. A compound of formula (I)

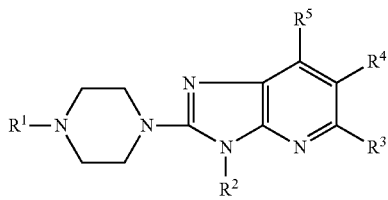

including any stereochemically isomeric form thereof, wherein
$R^1$ is hydrogen, phenylmethyl, pyridinylmethyl or benzo[1,3]dioxolylmethyl;
$R^2$ is $C_{1-4}$-alkyl;
$R^3$ is hydrogen, halo or $C_{1-4}$alkyl;
$R^4$ is hydrogen, halo or $C_{1-4}$alkyl; and
$R^5$ is hydrogen, amino, $C_{1-4}$alkylamino or di($C_{1-4}$alkyl)amino;
or a pharmaceutically acceptable acid addition salt thereof, or a solvate thereof.

2. The compound as claimed in claim 1 wherein $R^1$ is hydrogen.

3. The compound as claimed in claim 1 wherein $R^1$ is phenylmethyl.

4. The compound as claimed in claim 1 wherein $R^2$ is methyl.

5. The compound as claimed in claim 1 wherein the compound is 2-(4-benzyl-piperazin-1-yl)-3-methyl-3H-imidazo[4,5-b]pyridine or a pharmaceutically acceptable acid addition salts thereof.

6. A pharmaceutical composition comprising a pharmaceutically acceptable carrier and a therapeutically active amount of a compound according to claim 1.

7. A process for preparing a pharmaceutical composition comprising mixing a therapeutically active amount of a compound according to claim 1 with a pharmaceutically acceptable carrier.

8. A method of treating gastro-oesophageal reflux, heartburn, dyspepsia, early satiety, bloating or anorexia, comprising administering to a patient in need thereof an effective amount of a compound according to claim 1.

9. A process for preparing a compound of formula (I) wherein a) an intermediate of formula (II) is N-alkylated with an intermediate of formula (III), in a reaction-inert solvent

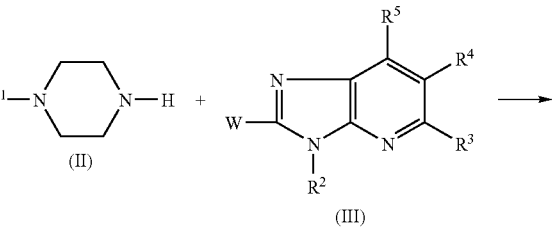

b) or; an intermediate of formula (IV) is N-alkylated with compound of formula (I a) in a reaction-inert solvent

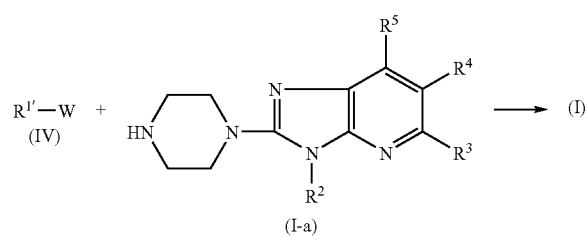

wherein in the above reaction schemes the radicals $R^{1'}$ is phenylmethyl, pyridinylmethyl or benzo[1,3]dioxolylmethyl, and $R^2$, $R^3$, $R^4$ and $R^5$ are as defined in claim 1 and W is an appropriate leaving group;

c) or; if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

10. A method of relaxing the fundus of a patient, comprising administering to said patient an effective amount of a compound according to claim 1.

11. A method of treating hampered or impaired relaxation of the fundus of a patient, comprising administering to said patient an effective amount of a compound according to claim 1.

* * * * *